(12) United States Patent
Vandewalle

(10) Patent No.: US 10,413,326 B2
(45) Date of Patent: *Sep. 17, 2019

(54) CANNULATED SYRINGE

(71) Applicant: BIOMET MANUFACTURING, LLC, Warsaw, IN (US)

(72) Inventor: Mark V. Vandewalle, Pierceton, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 607 days.

This patent is subject to a terminal disclaimer.

(21) Appl. No.: 14/288,450

(22) Filed: May 28, 2014

(65) Prior Publication Data

US 2014/0276596 A1 Sep. 18, 2014

Related U.S. Application Data

(63) Continuation of application No. 12/917,259, filed on Nov. 1, 2010, now Pat. No. 8,905,996.

(51) Int. Cl.
*A61B 17/34* (2006.01)

(52) U.S. Cl.
CPC .... *A61B 17/3472* (2013.01); *A61B 2017/347* (2013.01)

(58) Field of Classification Search
CPC ......... A61B 17/3472; A61B 2017/347; A61M 5/31; A61M 5/315
See application file for complete search history.

(56) References Cited

U.S. PATENT DOCUMENTS

| | | | | |
|---|---|---|---|---|
| 2,893,395 | A * | 7/1959 | Buck | A61B 5/0215 |
| | | | | 604/533 |
| 3,957,052 | A * | 5/1976 | Topham | A61M 1/0005 |
| | | | | 604/135 |
| 4,063,555 | A * | 12/1977 | Ulinder | A61M 39/02 |
| | | | | 137/583 |
| 4,274,408 | A | 6/1981 | Nimrod | |
| 4,451,257 | A * | 5/1984 | Atchley | A61M 1/0043 |
| | | | | 251/325 |
| 4,573,448 | A * | 3/1986 | Kambin | A61B 17/3417 |
| | | | | 128/898 |

(Continued)

FOREIGN PATENT DOCUMENTS

| | | |
|---|---|---|
| DE | 4136050 A1 | 5/1993 |
| WO | WO-2007029998 A2 | 3/2007 |

*Primary Examiner* — Bradley J Osinski
*Assistant Examiner* — Matthew A Engel
(74) *Attorney, Agent, or Firm* — Schwegman Lundberg & Woessner, P.A.

(57) ABSTRACT

A set of instruments configured to deliver a therapy to a bone can include a cannulated syringe. The cannulated syringe can extend along a longitudinal axis between a proximal and a distal end. The cannulated syringe can have an inner tube and an outer tube that are interconnected at the distal end as a single fixed unit. A first cannulation can be formed along the longitudinal axis of the cannulated syringe within the inner tube and a second cannulation can be formed within an annular space between the inner and outer tubes. The outer tube can define an opening through a sidewall thereof. The cannulated syringe can be closed from fluid communication between the inner and outer tubes.

20 Claims, 10 Drawing Sheets

(56) References Cited

U.S. PATENT DOCUMENTS

| | | | |
|---|---|---|---|
| 4,573,966 A * | 3/1986 | Weikl | A61M 25/1011 604/101.05 |
| 4,609,370 A * | 9/1986 | Morrison | A61B 17/3401 600/567 |
| 4,706,670 A * | 11/1987 | Andersen | A61L 29/06 604/526 |
| 4,813,938 A | 3/1989 | Raulerson | |
| 4,968,306 A * | 11/1990 | Huss | A61M 25/007 604/264 |
| 5,013,300 A * | 5/1991 | Williams | A61M 1/008 433/91 |
| 5,176,647 A * | 1/1993 | Knoepfler | A61M 25/06 604/158 |
| 5,178,611 A * | 1/1993 | Rosenberg | A61M 25/0017 604/158 |
| 5,250,055 A * | 10/1993 | Moore | A61B 17/0469 128/898 |
| 5,300,022 A * | 4/1994 | Klapper | A61M 1/0084 604/264 |
| 5,312,360 A * | 5/1994 | Behl | A61B 17/34 604/104 |
| 5,320,611 A * | 6/1994 | Bonutti | A61B 17/0401 604/264 |
| 5,324,276 A * | 6/1994 | Rosenberg | A61M 25/0017 604/172 |
| 5,370,647 A * | 12/1994 | Graber | A61B 17/00234 606/127 |
| 5,396,880 A * | 3/1995 | Kagan | A61B 1/0051 600/109 |
| 5,464,407 A * | 11/1995 | McGuire | A61B 17/15 606/104 |
| 5,514,100 A * | 5/1996 | Mahurkar | A61M 5/322 604/158 |
| 5,603,716 A * | 2/1997 | Morgan | A61B 17/1635 128/898 |
| 5,665,092 A * | 9/1997 | Mangiardi | A61B 17/3472 604/104 |
| 5,718,707 A | 2/1998 | Mikhail | |
| 5,735,813 A | 4/1998 | Lewis | |
| 5,755,721 A * | 5/1998 | Hearn | A61B 17/1728 606/104 |
| 5,800,375 A * | 9/1998 | Sweezer | A61M 1/10 604/101.05 |
| 5,800,407 A * | 9/1998 | Eldor | A61M 25/007 604/264 |
| 5,873,851 A * | 2/1999 | Nilsson | A61M 1/0084 604/22 |
| 6,132,396 A * | 10/2000 | Antanavich | A61B 17/00491 141/18 |
| 6,202,898 B1 * | 3/2001 | Koch | A61M 3/0233 222/400.7 |
| 6,371,944 B1 | 4/2002 | Liu et al. | |
| 6,395,007 B1 | 5/2002 | Bhatnagar et al. | |
| 6,447,515 B1 * | 9/2002 | Meldrum | A61B 17/7258 606/323 |
| 6,530,880 B2 * | 3/2003 | Pagliuca | A61B 1/00154 600/102 |
| 6,575,979 B1 * | 6/2003 | Cragg | A61B 17/1671 606/279 |
| 6,652,528 B2 | 11/2003 | Vandewalle | |
| 6,752,809 B2 | 6/2004 | Gorek | |
| 6,770,079 B2 | 8/2004 | Bhatnagar et al. | |
| 6,887,246 B2 | 5/2005 | Bhatnagar et al. | |
| 7,141,054 B2 | 11/2006 | Vandewalle | |
| 7,226,451 B2 | 6/2007 | Shluzas et al. | |
| 7,309,338 B2 * | 12/2007 | Cragg | A61B 17/1671 606/279 |
| 7,329,259 B2 * | 2/2008 | Cragg | A61B 17/1671 606/279 |
| 7,530,982 B1 | 5/2009 | Goshert | |
| 7,572,244 B2 * | 8/2009 | Weisel | A61B 17/22 604/27 |
| 7,789,846 B2 * | 9/2010 | Solar | A61F 7/12 604/113 |
| 7,850,730 B2 * | 12/2010 | Vresilovic | A61F 2/4611 606/86 R |
| 7,909,873 B2 * | 3/2011 | Tan-Malecki | A61B 17/1617 606/86 R |
| 7,914,535 B2 * | 3/2011 | Assell | A61B 17/7074 606/279 |
| 7,942,826 B1 * | 5/2011 | Scholl | A61B 5/0492 600/554 |
| 7,955,312 B2 * | 6/2011 | Miller | A61B 17/3478 604/104 |
| 7,959,637 B2 * | 6/2011 | Fox | A61B 17/155 606/87 |
| 8,062,246 B2 * | 11/2011 | Moutafis | A61B 17/3203 604/22 |
| 8,518,087 B2 * | 8/2013 | Lopez | A61B 18/1487 606/279 |
| 8,905,996 B2 * | 12/2014 | Vandewalle | A61B 17/3472 604/239 |
| 9,241,811 B2 * | 1/2016 | Davenport | A61F 2/4603 |
| 2003/0100849 A1 * | 5/2003 | Jang | A61M 25/0023 600/585 |
| 2004/0186471 A1 * | 9/2004 | Trieu | A61F 2/441 606/914 |
| 2006/0253081 A1 | 11/2006 | Paulos et al. | |
| 2008/0071281 A1 * | 3/2008 | Wilson | A61F 2/4611 606/92 |
| 2008/0228189 A1 * | 9/2008 | Fox | A61B 17/1764 606/88 |
| 2008/0269762 A1 * | 10/2008 | Simon | A61B 17/56 606/99 |
| 2009/0149860 A1 | 6/2009 | Scribner et al. | |
| 2009/0264942 A1 * | 10/2009 | Beyar | A61B 17/7095 606/86 R |
| 2009/0326538 A1 * | 12/2009 | Sennett | A61B 17/1642 606/80 |
| 2012/0109102 A1 * | 5/2012 | Vandewalle | A61B 17/3472 604/506 |
| 2013/0178859 A1 * | 7/2013 | Fox | A61B 17/1764 606/87 |
| 2014/0081278 A1 * | 3/2014 | Witt | A61F 2/4609 606/91 |
| 2014/0081282 A1 * | 3/2014 | Davenport | A61F 2/4603 606/99 |
| 2014/0276596 A1 * | 9/2014 | Vandewalle | A61B 17/3472 604/506 |

\* cited by examiner

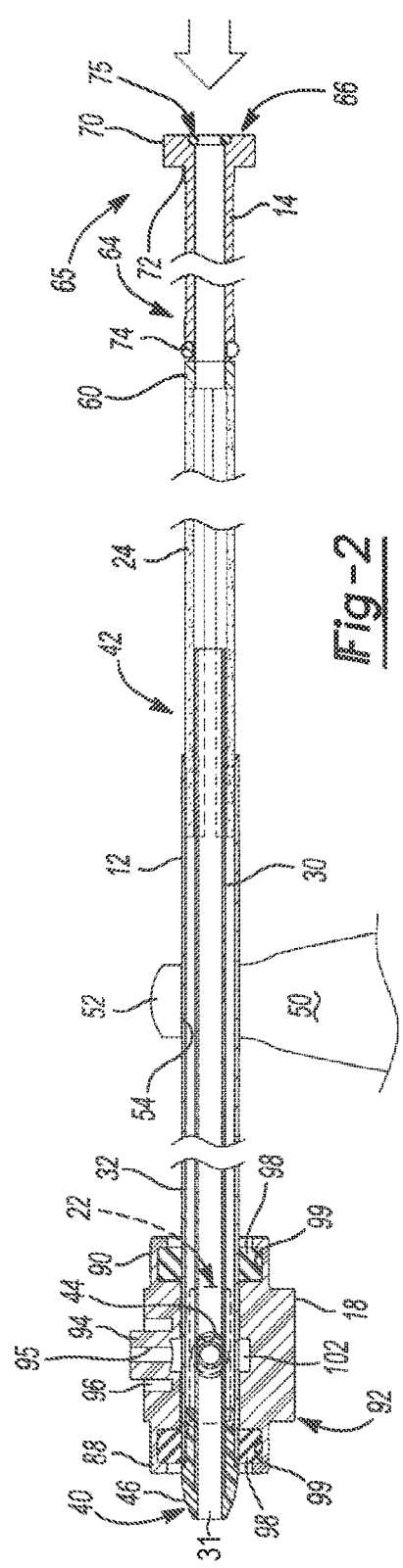
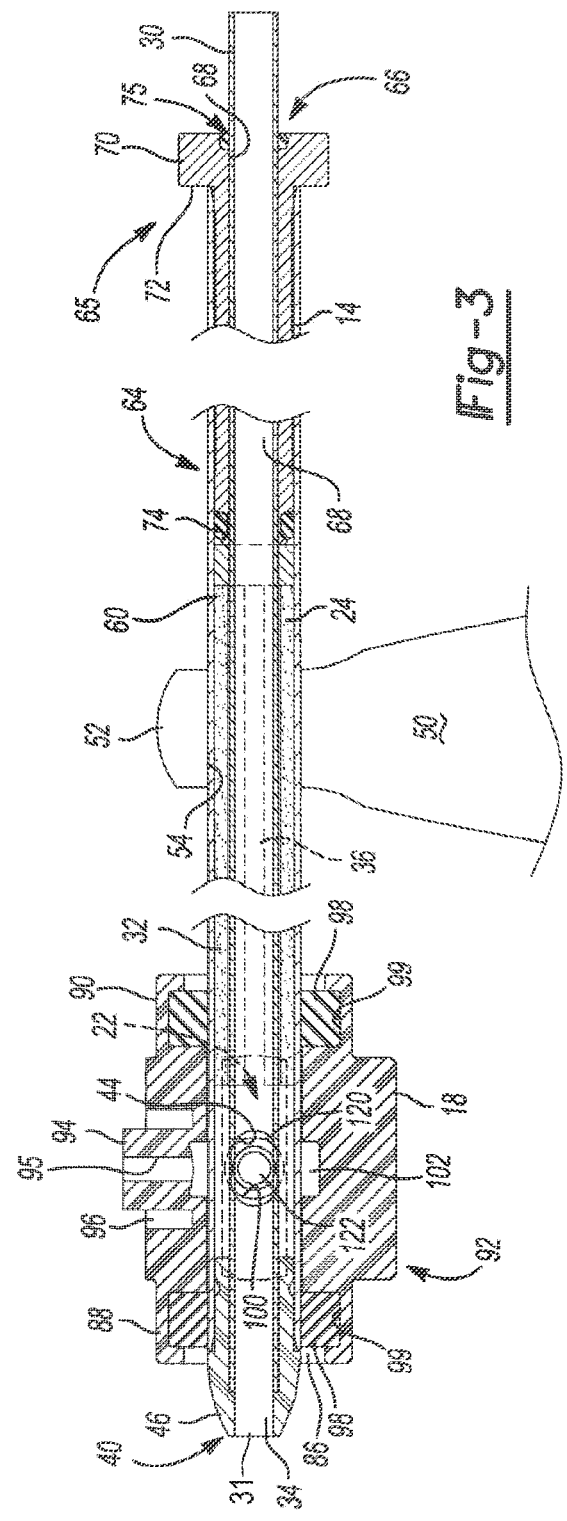

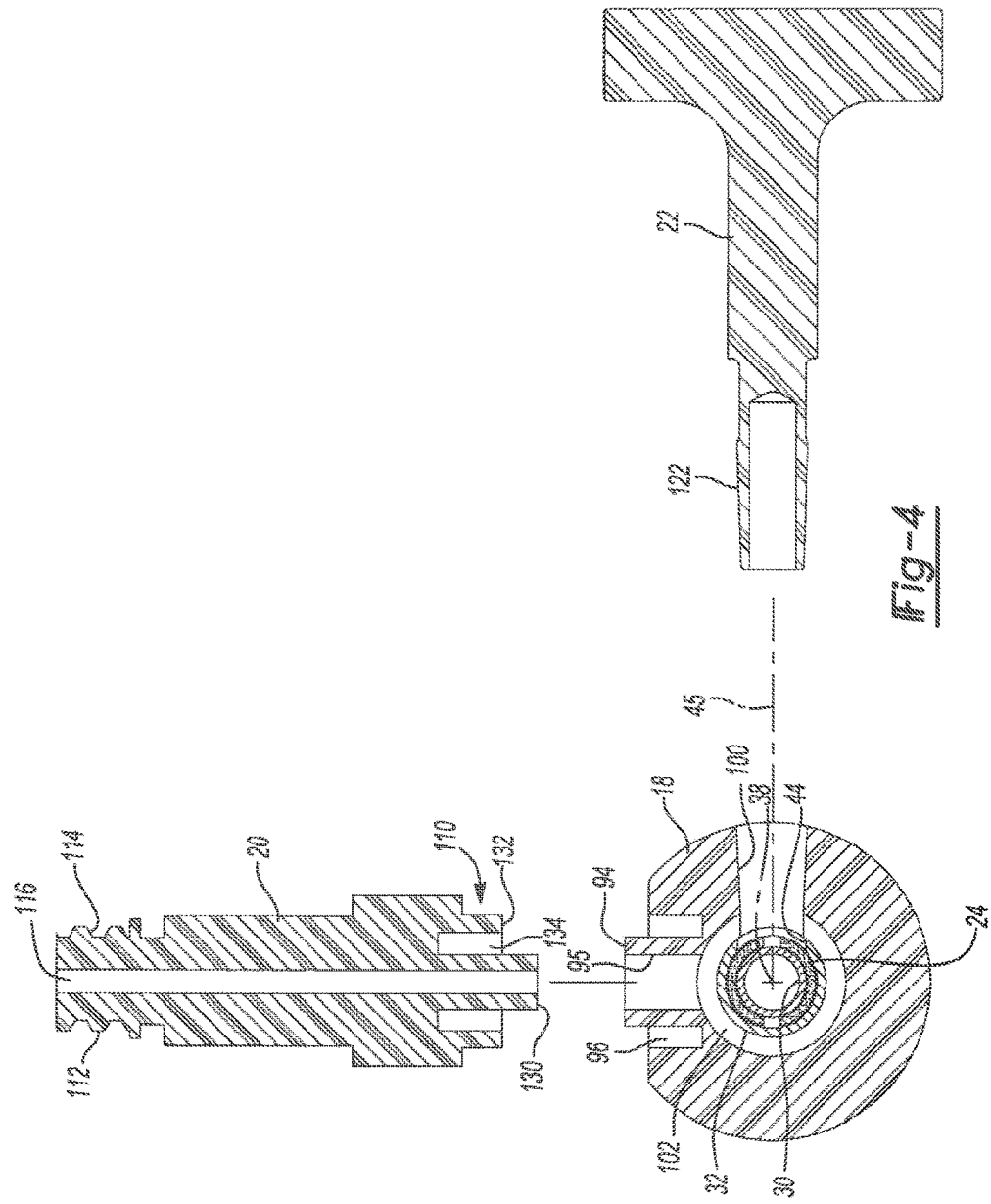

CANNULATED SYRINGE

CROSS-REFERENCE TO RELATED APPLICATION

This application is a continuation of U.S. application Ser. No. 12/197,259 filed Nov. 1, 2010. The disclosure of the above application is incorporated herein by reference.

INTRODUCTION

The present technology relates generally to biologic material delivery systems and more specifically to a set of instruments and related method for delivering biologic material to a bone.

In some instances during treatment of fractures on various long bones, such as diaphyseal fractures of the femur, tibia and humerus bones, it may be desirable to introduce a flowable biologic material through the IM (IM) canal of the bone. The biologic material can be introduced alone, or in combination with an IM nail. In this regard, an IM nail can have an elongated metallic member that includes one or more cylindrical cavities that can be perpendicular to the long axis of the IM nail for receiving a fastener element, such as a transcortical screw. The IM nail can be positioned within the medullary cavity and can be secured to the proximal and distal fracture segments using transcortical screws, which penetrate both cortices of the bone, as well as pass through the cylindrical cavities formed in the IM nail.

According to one surgical technique, a guide wire can be located into the IM canal past the fracture. A cannulated reamer can then locate around the guide wire to ream the IM canal for placement of the IM nail. The guide wire can also be used to guide the IM nail into position once the IM canal has been sufficiently reamed. As identified above, in some examples, it may be desired to also introduce biologic material into the IM canal around the fracture prior to implanting the IM nail. In some cases, it can be challenging to introduce biologic material near the fracture site while isolating the guide wire from contact with the biologic material and leaving the guide wire in place for later reference of the IM nail. Additionally, it is undesirable to remove the guide wire after reaming and reintroducing it to guide the insertion of the IM nail.

SUMMARY

A set of instruments configured to deliver a therapy to a bone can include a cannulated syringe. The cannulated syringe can extend along a longitudinal axis between a proximal and a distal end. The cannulated syringe can have an inner tube and an outer tube that are interconnected at the distal end as a single fixed unit. A first cannulation can be formed along the longitudinal axis of the cannulated syringe within the inner tube and a second cannulation can be formed within an annular space between the inner and outer tubes. The outer tube can define an opening through a sidewall thereof. The cannulated syringe can be closed from fluid communication between the inner and outer tubes.

According to additional features, the opening in the outer tube can include an oblong slot. The inner tube can be longer than the outer tube, such that the inner tube extends proud from the proximal end relative to the outer tube. The cannulated syringe can further include a handle that is disposed on the proximal end and that extends generally transverse to the longitudinal axis.

The set of instruments can further include a plunger that has a tubular body that is configured to slidably advance through the second cannulation in a direction toward the distal end. The plunger can have a gripping portion that is disposed on a proximal end thereof. The set of instruments can further include a piston that has a tubular body that is configured to slidably advance through the second cannulation upon urging from the plunger.

The set of instruments can further comprise a valve body and a locking member. The valve body can have a central passage that is sized to slidably advance onto the distal end of the cannulated syringe in an operating position. The valve body can have a locking aperture and a valve inlet formed thereon. The valve inlet can be adapted to fluidly connect with the opening of the outer tube in the operating position. The locking member can be adapted to selectively locate through the locking aperture of the valve body and into the opening of the outer tube thereby inhibiting slidable translation of the valve body along the outer tube of the cannulated syringe.

The valve body can have an annular channel formed around an inner diameter that fluidly connects the valve inlet and the opening in the outer tube of the cannulated syringe in the operating position. The locking member can be adapted to create a fluid tight seal at the locking aperture in an installed position. The locking member can have a distal end that has a cross-section less than the opening in the outer tube, such that fluid is permitted to pass through the opening in the outer tube when the locking member is in the installed position.

The set of instruments can further include a plug that has a tubular body that is configured to slidably advance through the second cannulation in a direction toward the distal end. The plug can have a collar on a proximal end that is adapted to engage a proximal terminal end of the outer tube in an advanced position while the inner tube locates through the tubular body of the plug. The plug can further include elastomeric seals at distal and proximal ends that are adapted to form a fluid tight seal between the inner and outer tubes in the advanced position. According to some examples, a valve attachment can be disposed on the valve body that fluidly connects to the valve inlet. The valve attachment can have threads formed thereon that are adapted to threadably mate with a fluid delivery device.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2 is a cross-sectional view of the cannulated syringe, valve body and plug shown during initial introduction of a biologic material into an outer cannulation defined by the cannulated syringe;

FIG. 3 is a cross-sectional view of the cannulated syringe, valve body and plug shown with the plug advanced to a sealing position into the proximal end of the cannulated syringe;

FIG. 4 is an exploded cross-sectional view of the valve member, a valve attachment and a locking member of the instrument set shown in FIG. 1;

Figure 10:
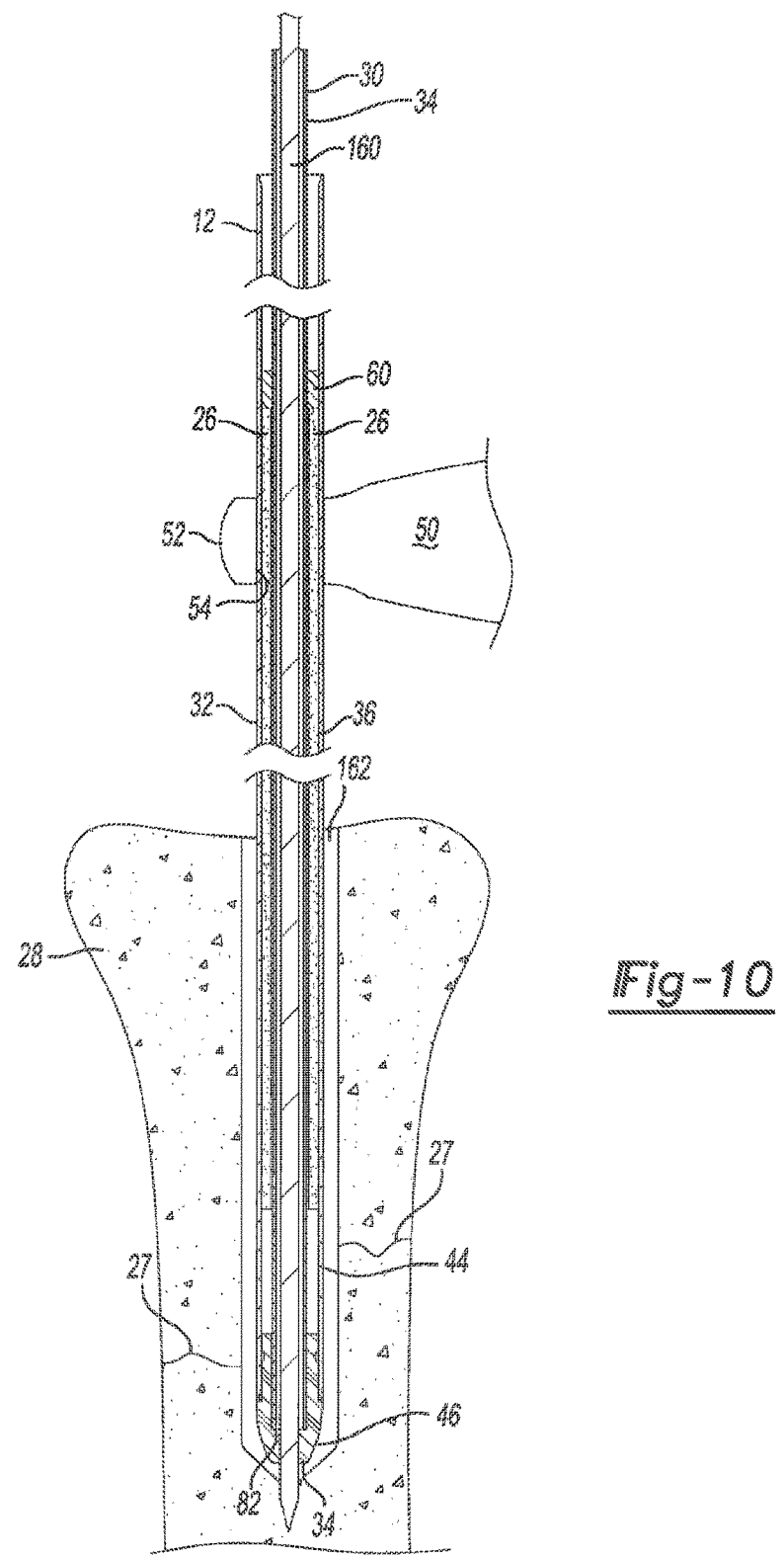
Figure 11:
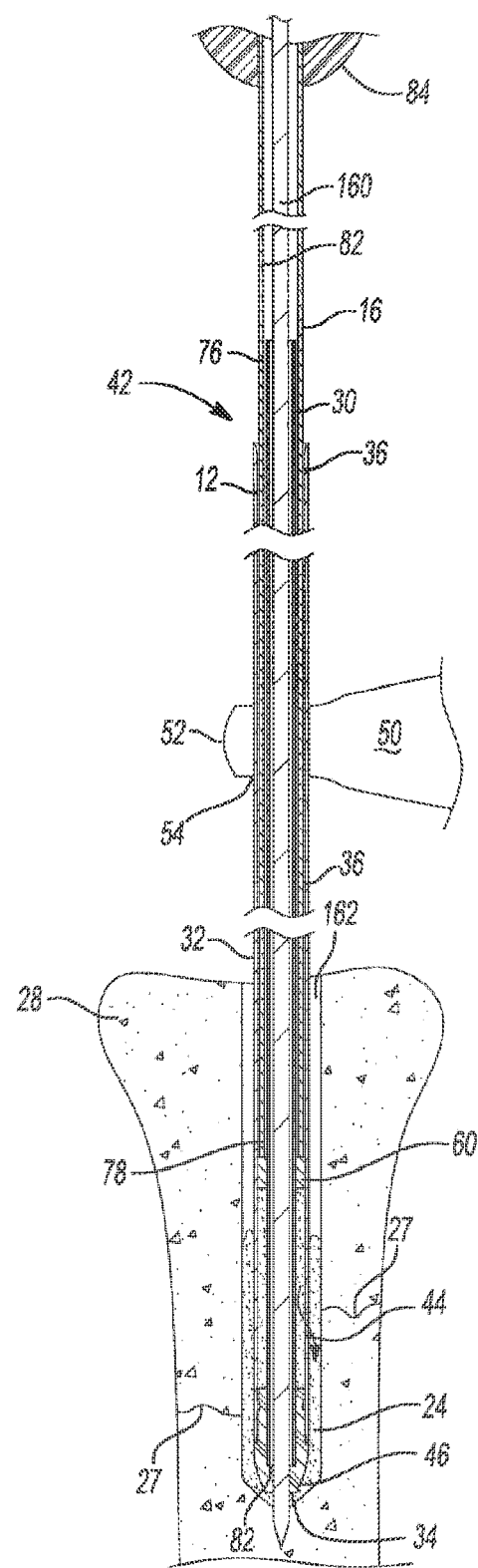

FIG. 10 is a cross-sectional view of the cannulated syringe shown advanced over a guide wire extending from an IM canal of a tibia; and FIG. 11 is a cross-sectional view of the cannulated syringe of FIG. 10 and shown with a plunger being advanced toward the distal end of the cannulated syringe, such that the biologic material is expelled through an opening formed in an outer tube of the cannulated syringe.

Corresponding reference numerals indicate corresponding parts throughout the several views of the drawings.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Moreover, although the following description and illustrations refer specifically to an intraoperative introduction of biologic material during an IM (IM) nailing of a tibia, it will be understood that the instruments and related method disclosed herein may be applied to other applications. For example, the instruments disclosed herein may be used to introduce biologic material along an IM canal of other bones, such as a humerus or femur for example. Therefore, it will be understood that the present description and the claims are applicable to any appropriate bone in the body. A non-limiting discussion of terms and phrases intended to aid understanding of the present technology is provided at the end of this Detailed Description.

Figure 1:
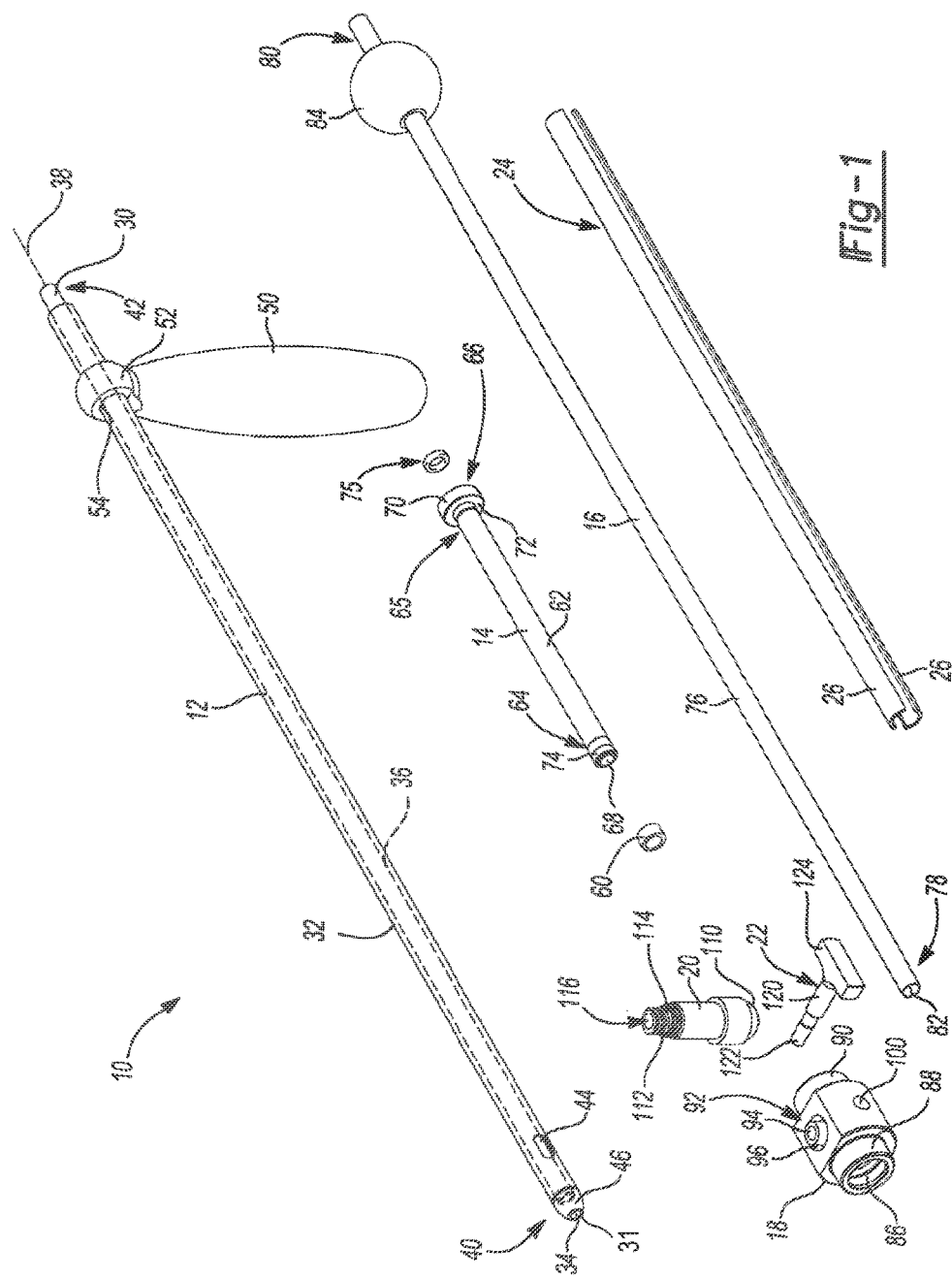
FIG. 1 is an exploded perspective view of an instrument set configured to deliver a therapy to a bone constructed in accordance to one example of the present teachings.

With initial reference to FIG. 1, an instrument set that may be used during intraoperative introduction of biologic material into bone, such as during an IM nailing is shown and generally identified at reference numeral 10. The instrument set 10 can generally include a cannulated syringe 12, a plug 14, a plunger 16, a valve body 18, a valve attachment 20 and a locking member 22. By way of example, injectable material 24 is shown in a freeze-dried state and can include any biologic material that can facilitate healing, such as demineralized bone matrix (DBM). The injectable material 24 is illustrated as generally having a pair of half cylindrical troughs 26. As will become appreciated more fully from the following discussion, the instrument set 10 can be used to initially hydrate the freeze-dried DBM and subsequently expel the injectable material 24 at a desired delivery site, such as adjacent to fractures 27 in the tibia 28 (see FIGS. 10 and 11).

The cannulated syringe 12 can generally include an inner tube 30 and an outer tube 32. The outer tube 32 can be radially stepped outwardly from the inner tube 30. The outer tube 32 including a first opening 31 at a distal end 40. The cannulated syringe 12 can therefore provide a dual cannulation with an inner cannulation 34 defined within the inner tube 30 and an outer cannulation 36 defined by the annular space created between the inner tube 30 and the outer tube 32. The cannulated syringe 12 can generally extend along a longitudinal axis 38 between the distal end 40 and a proximal end 42. The distal end 40 can be defined as any portion of the cannulated syringe 12 that is at the distal opening (e.g., the first opening 31) of the inner cannulation 34 or a distance proximal therefrom.

A tapered distal tip 46 can be formed at the distal end 40 that generally connects the inner tube 30 with the outer tube 32. In some examples, the tapered distal tip 46 can be a separate piece that is connected to both of the inner and outer tubes 30 and 32. The tapered distal tip 46 can be connected in any manner such that a fluid tight seal is created between the inner and outer tubes 30 and 32 at the distal end 40. In this regard, the cannulated syringe 12 is closed from fluid communication between the inner and outer tubes 30 and 32.

An opening 44 (also referred to as second opening 44) can be formed at the distal end 40. In one example, the second opening 44 can be formed through the outer tube 32. The second opening 44 can be formed at any distance proximal from the distal opening of the inner cannulation 34 and the first opening 31. In one example, the second opening 44 can be provided at a location within the distal most one-quarter of the entire length of the cannulated syringe 12. In some examples, the second opening 44 can be additionally or alternatively formed through the tapered distal tip 46. In the exemplary configuration, a centerpoint of the second opening 44 is located at a distance measured from the distal opening (e.g., the first opening 31) of the inner cannulation 34 to about one-fifteenth of the entire length of the cannulated syringe 12. The second opening 44 can be non-circular such as an oblong slot for example. In one example, the second opening 44 can extend between about three-quarters of an inch and one inch from the distal opening (e.g., the first opening 31) of the inner cannulation 34. Other configurations are contemplated. The second opening 44 can generally extend along an axis 45 (FIG. 4) that is non-parallel to and intersects the longitudinal axis 38. Other shapes and configurations are contemplated.

In one example, the inner tube 30 can extend proud from the outer tube 32 at the proximal end 42. A handle 50 can be fixedly connected near the proximal end 42 of the cannulated syringe 12. In one example, the handle 50 can have a looped connection portion 52 that defines an opening 54 that receives the outer tube 32 of the cannulated syringe 12. Other configurations are contemplated. In some examples, the cannulated syringe 12 can further include a piston 60 slidably mounted in the outer cannulation 36 between the inner tube 30 and the outer tube 32. The piston 60 can have a ring-like shape that has a cross-section that substantially matches the outer cannulation 36 for slidable communication therewithin (see FIG. 3). A seal or o-ring can be additionally or alternatively incorporated relative to the piston 60.

The plug 14 will now be described in greater detail. The plug 14 can be used to create a fluid tight seal in the outer cannulation 36 at the proximal end 42 of the cannulated syringe during an evacuation and hydration sequence of the injectable material 24 as will become appreciated from the following discussion. The plug 14 can generally have a plug body 62 that extends between a distal end 64 and a proximal end 66. The plug body 62 can define a central passage 68 that extends along the entire length of the plug body 62 for receiving the inner tube 30. The plug 14 can also include a collar 70 provided at the proximal end 66. The collar 70 can have a radial ledge 72 that can have an outer diameter that is greater than the outer tube 32. Seals or o-rings 74 and 75 can be disposed around the distal end 64 and proximal end 65 of the plug 14.

The plunger 16 can generally include a tubular body 76 that extends between a distal end 78 and a proximal end 80. The plunger 16 can be used to expel the injectable material 24 through the second opening 44 as will be discussed herein. The tubular body 76 can define a cannulation 82 that extends along the entire length of the plunger 16 for receiving the inner tube 30. A gripping portion 84 can be disposed near the proximal end 80 of the tubular body 76.

With continued reference to FIG. 1 and additional references to FIGS. 2 and 3, the valve body 18 will be further described. The valve body 18 can define a central passage 86 that can be adapted to slidably accept the cannulated syringe 12 therethrough as will be described in detail herein. The valve body 18 can further include a distal sleeve portion 88 and a proximal sleeve portion 90. The valve body 18 can have a valve attachment mounting portion 92 that has a valve inlet body 94 extending therefrom. The valve inlet body 94 can define a valve inlet 95. A cylindrical pocket 96 can be provided on the valve attachment mounting portion 92 around the valve inlet body 94. A pair of seals or o-rings 98 can be received in respective annular pockets 99 formed around an inner diameter of the valve body 18 at the distal sleeve portion 88 and the proximal sleeve portion 90. A locking aperture 100 can be formed through the valve body 18 that connects the outer surface of the valve body 18 with the central passage 86. The valve body 18 can include an inner annular channel 102 (see FIG. 4) that generally connects the valve inlet 95 and the locking aperture 100 in fluid communication. As will be described further herein, the annular channel 102 can provide a fluid connection between the valve inlet 95 of the valve body 18 and the second opening 44 formed in the outer tube 32 of the cannulated syringe 12.

The valve attachment 20 can generally include a valve mating portion 110 on one end and a male connection portion 112 on an opposite end. The male connection portion 112 can define threads 114 therealong. The valve attachment 20 can generally define an injection port 116 therethrough. The locking member 22 can generally include a body 120 in the shape of a "T" that has a tapered distal tip 122 and a handle 124 (as best illustrated in FIG. 1).

An exemplary method of using the instrument set 10 during a surgical technique to deliver biologic material around a tibial fracture will be described. At the outset, a surgeon can select a desired injectable material 24, such as the freeze-dried DBM discussed above. With the piston 60 removed from the outer cannulation 36 of the cannulated syringe 12, the injectable material 24 can be initially advanced into the proximal end 42 of the cannulated syringe 12 into the outer cannulation 36. While the injectable material 24 is shown generally as opposing cylindrical troughs in a pre-cast or freeze-dried state, the injectable material 24 can take a variety of shapes and forms. For example, the injectable material 24 can be a continuous cylindrical member or a collection of more than two partial segments of injectable material 24. Moreover, while the injectable material 24 has been illustrated as having a length that extends a distance that is generally greater than half of the cannulated syringe 12, the injectable material 24 can be any length that provides enough biologic material that is suitable for a particular patient. Furthermore, the injectable material 24 can additionally or alternatively be in a flowable or partially flowable state such that a surgeon can shape the injectable material 24 as needed.

Once the injectable material 24 has been loaded into the outer cannulation 36 at the proximal end 42 of the cannulated syringe 12, the piston 60 can be loaded into the outer cannulation 36 at the proximal end 42 of the cannulated syringe 12 (see FIGS. 2 and 3).

The plug 14 can then be used to further advance the injectable material 24 toward the distal end 40 of the cannulated syringe 12. Specifically, the distal end 64 of the plug 14 can be initially advanced to a position adjacent the proximal end 42 of the cannulated syringe 12 until the inner tube 30 locates into the central passage 68 of the plug 14. The plug 14 can then be further advanced toward the distal end 40 of the cannulated syringe 12, such that the plug body 62 locates progressively further into the outer cannulation 36 of the cannulated syringe 12. The plug 14 can be further advanced until the radial ledge 72 of the collar 70 abuts the outer tube 32 at the proximal end 42 of the cannulated syringe 12 (FIG. 3). The plug 14 can therefore provide a fluid tight seal near the proximal end 42 of the cannulated syringe 12 and more specifically proximally relative to the injectable material 24. The o-rings 74 and 75 arranged on the distal end 64 and proximal end 65 of the plug 14 alone or in combination with the piston 60 (and/or other supplemental seals, not shown) can facilitate formation of the fluid tight seal between the inner tube 30 and the outer tube 32 in the outer cannulation 36 at a location proximal relative to the injectable material 24.

Figure 5:
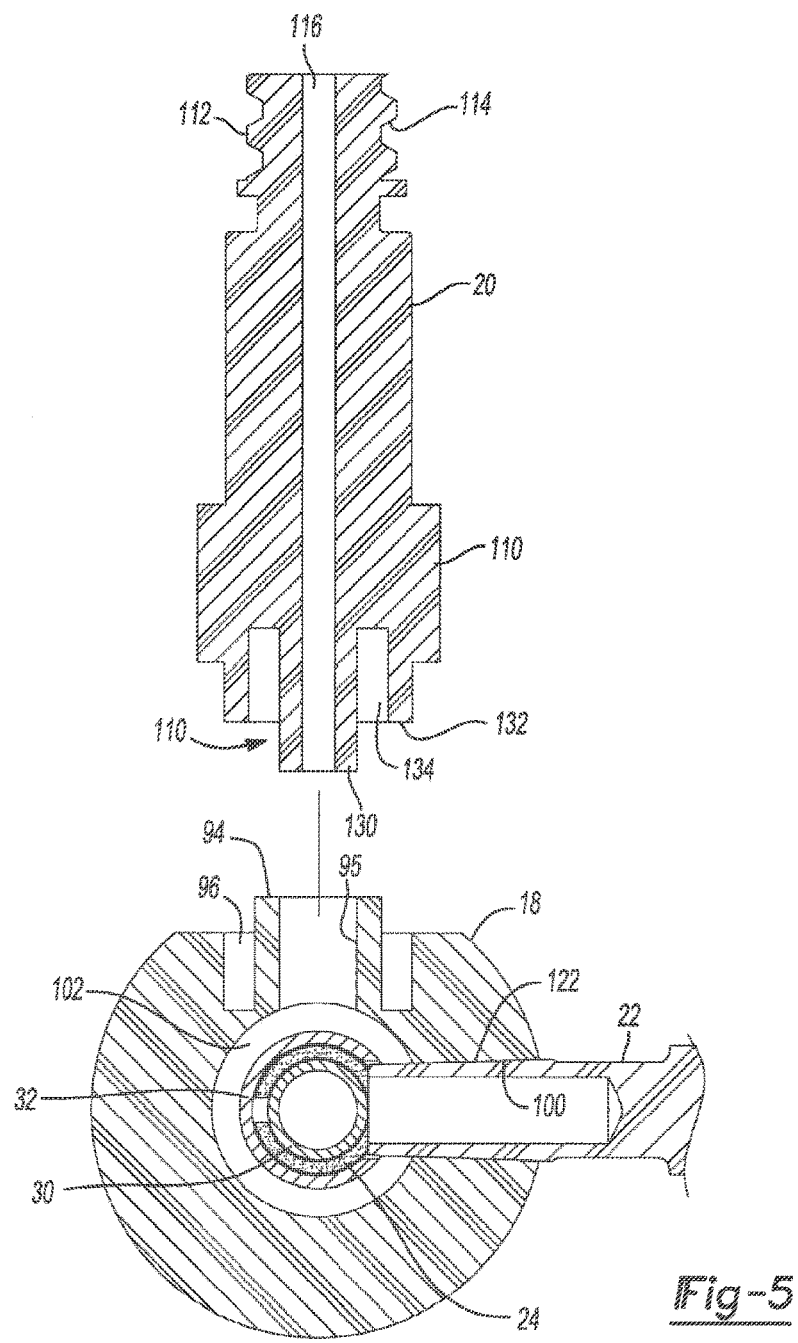
FIG. 5 is an exploded cross-sectional view of the valve member, valve attachment and locking member shown with a distal tip of the locking member located into a locking aperture of the valve body.

With reference now to FIGS. 1 and 4, the valve body 18 can be slidably advanced onto the distal end 40 of the cannulated syringe 12. In this regard, the tapered distal tip 46 of the cannulated syringe 12 can be advanced through the central passage 86 of the valve body 18 until the locking aperture 100 generally aligns with the second opening 44 of the outer tube 32 on the cannulated syringe 12. It is appreciated that the o-rings 98 engage the outer tube 32 and cooperate to provide a fluid tight seal at the distal sleeve portion 88 and the proximal sleeve portion 90. The tapered distal tip 122 of the locking member 22 can be advanced into the locking aperture 100 of the valve body 18 and through the opening 44 of the outer tube 32 on the cannulated syringe 12 (FIG. 5). Advancing the tapered distal tip 122 of the locking member 22 through the opening 44 can lock the valve body 18 from slidably advancing along the cannulated syringe 12.

The valve attachment 20 can then be coupled to the valve body 18. Those skilled in the art will readily appreciate that while the step of coupling the valve attachment 20 to the valve body 18 is being described in sequence, the valve attachment 20 may already be coupled to the valve body 18 previously. In this regard, in some examples the valve attachment 20 and the valve body 18 can be provided as a single unit. Nevertheless, inner and outer cylinders 130 and 132, respectively, provided at the valve mating portion 110 of the valve attachment 20 are advanced into a clearance fit (FIG. 16) with the valve inlet body 94 of the valve body 18. In this regard, the outer cylinder 132 can locate into the cylindrical pocket 96 formed in the valve body 18 while the valve inlet body 94 can locate into a cylindrical pocket 134 defined in the annular space between the inner cylinder 130 and the outer cylinder 132. In some examples, a flowable adhesive can be additionally applied at the interface between the valve attachment 20 and the valve body 18.

Figure 6:
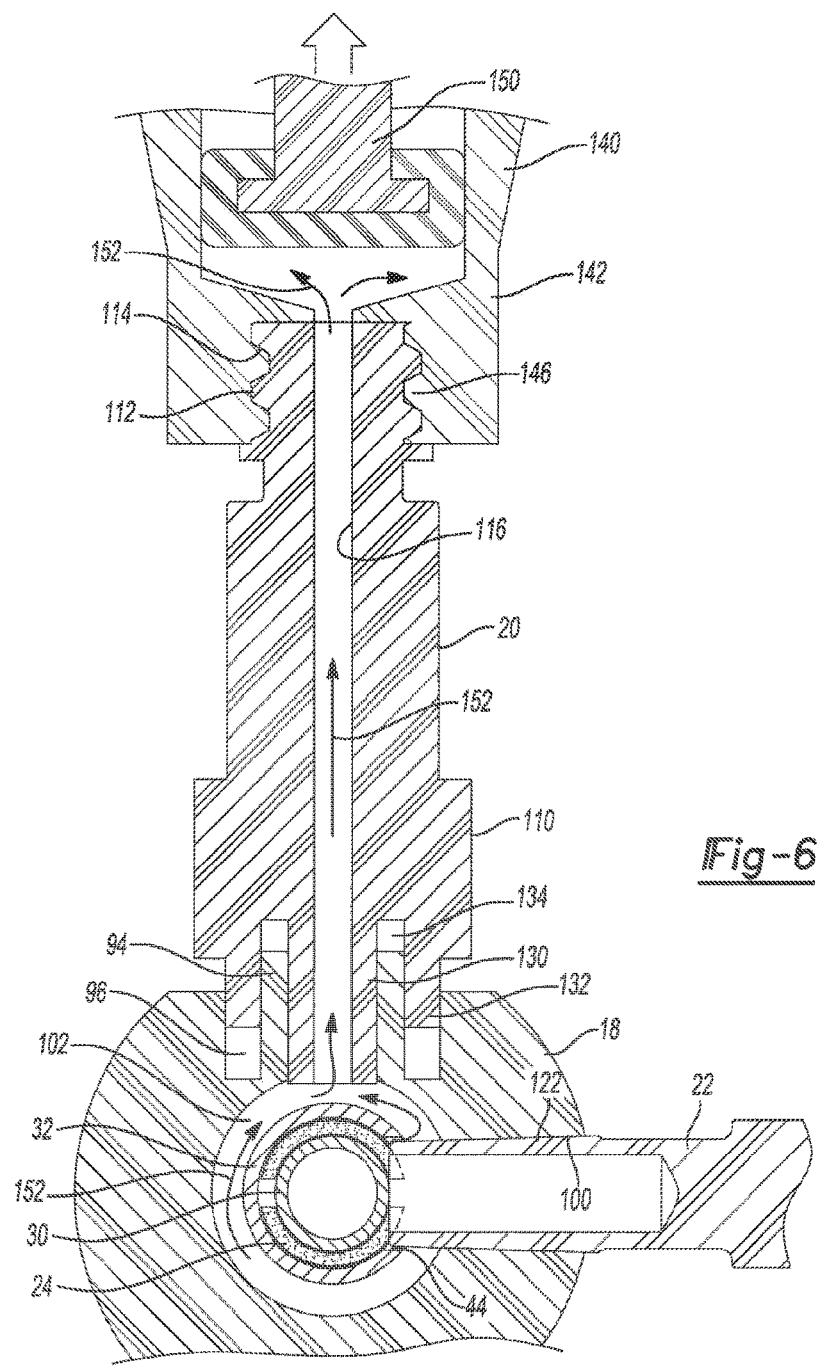
FIG. 6 is a cross-sectional view of the valve body and valve attachment shown with a syringe withdrawing air from the outer cannulation of the cannulated syringe.
Figure 7:
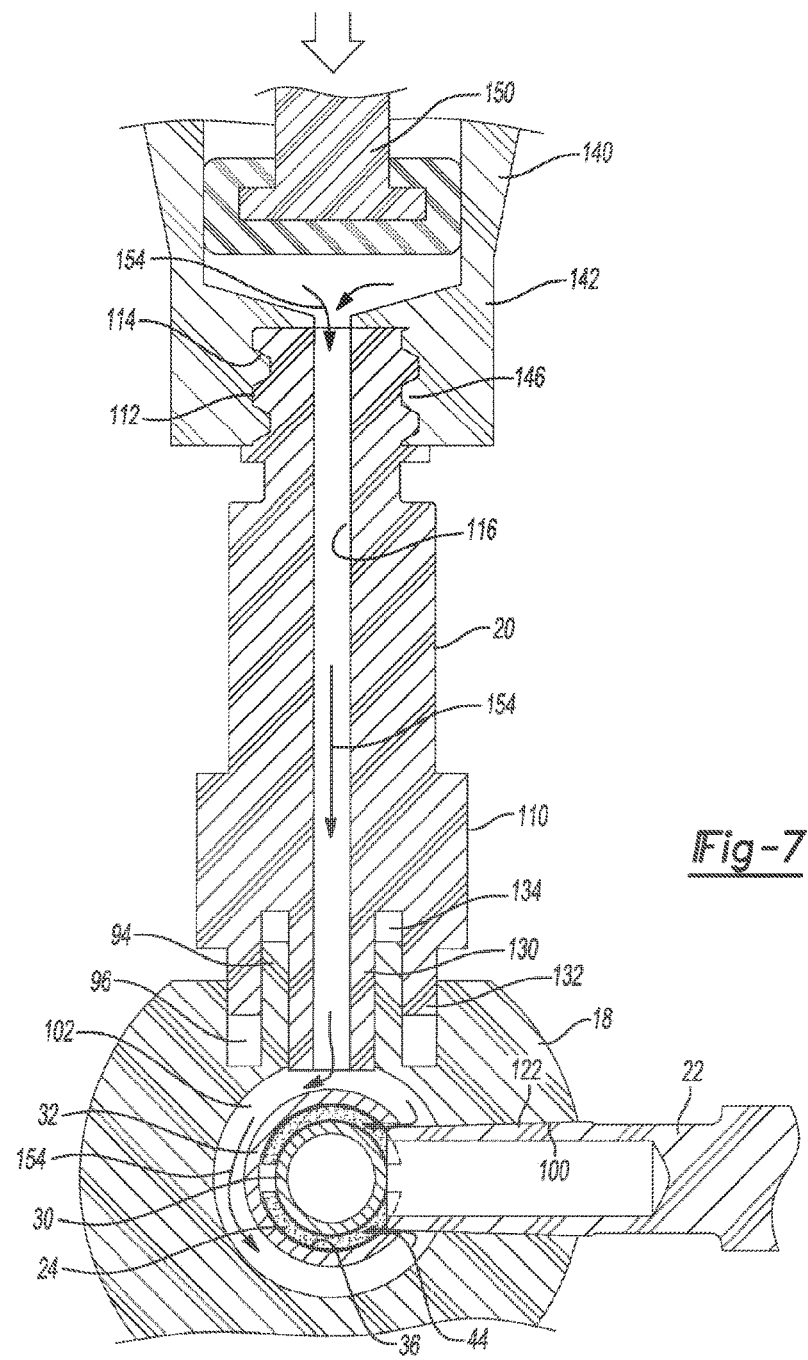
FIG. 7 is a cross-sectional view of the valve body, valve attachment and locking member shown with the syringe introducing a hydrating fluid into the outer cannulation of the cannulated syringe.
Figure 8:
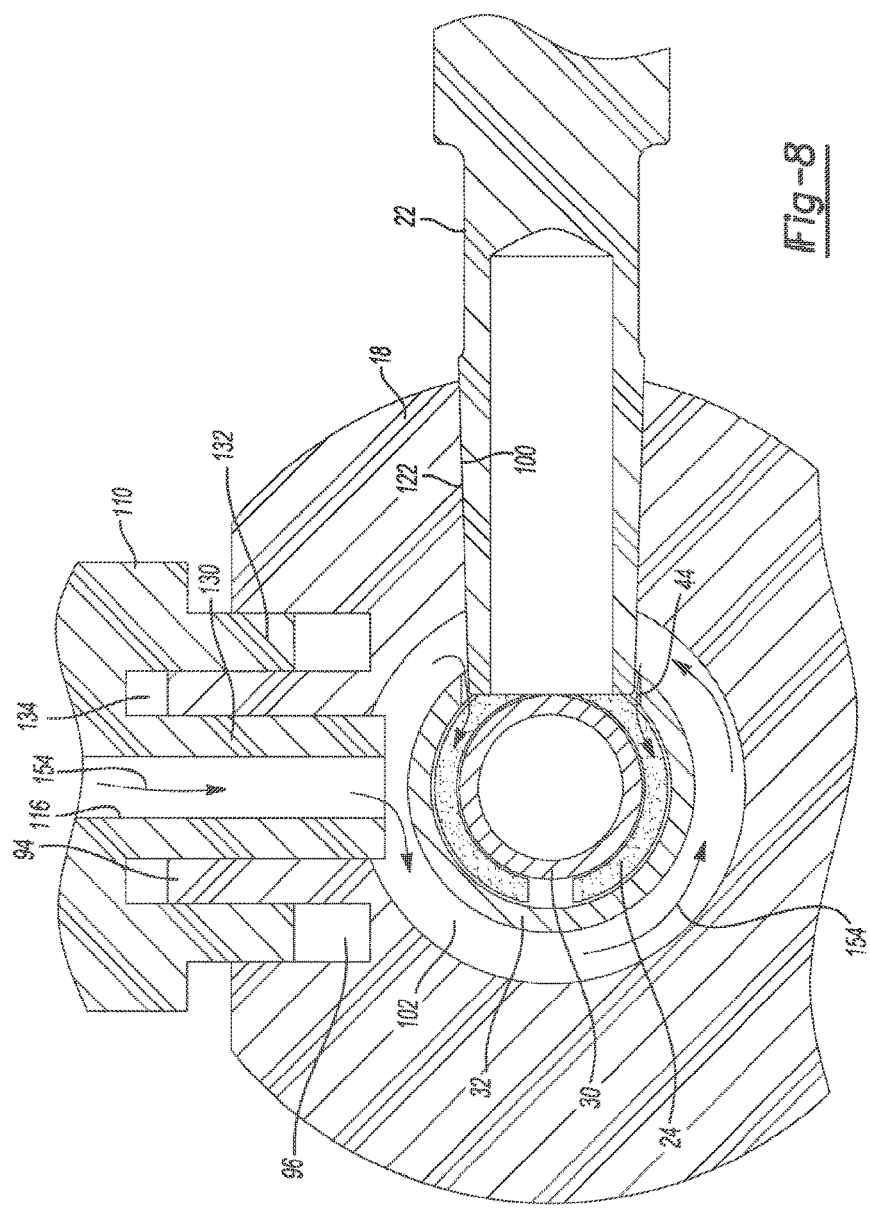
FIG. 8 is a detailed view of the valve body of FIG. 7 shown during introduction of the hydrating fluid into the outer cannulation of the cannulated syringe during hydration of the biologic material.

Turning now to FIGS. 6-8, the method will be further described. With the valve attachment 20 coupled to the valve body 18, an auxiliary syringe 140 can be fluidly connected to the valve attachment 20. For example, a female receiving portion 142 can fluidly connect to the auxiliary syringe 140 (such as directly as shown, or alternatively through a tube). The female receiving portion 142 can have threads 146 that threadably mate with the threads 114 on the male connection portion 112 of the valve attachment 20. It will be appreciated that the male threads 112 may alternatively be provided on the syringe 140 and the female threads 146 provided on the valve attachment 20. Other connections can be incorporated.

A plunger 150 associated with the auxiliary syringe 140 can be withdrawn, such that air 152 is encouraged to evacuate the outer cannulation 36 of the cannulated syringe 12. Explained in greater detail, retracting the plunger 150 away from the auxiliary syringe 140 can create a vacuum through the injection port 116, around the annular channel 102 in the valve body 18 through the second opening 44 in the outer tube 32 and ultimately within the outer cannulation 36 that houses the injectable material 24. Notably, while the tapered distal tip 122 of the locking member 22 extends through the second opening 44 in the outer tube 32, the second opening 44 is not fully blocked. In this regard, because the cross-section of the opening 44 is larger (i.e., oblong) than the cross-section of the tapered distal tip 122, fluid is still permitted to pass around the locking member 22 and through the second opening 44. At this time, the o-rings 74 and 75 on the plug 14 (and in some examples in combination with the piston 60) cooperates to preclude any air 152 from being communicated through the proximal end 42 of the cannulated syringe 12.

Once any remaining air 152 has been evacuated from the outer cannulation 36, the injectable material 24 can then be hydrated. In this regard, the auxiliary syringe 140 (or another fluid delivery device) can then be fluidly connected to the valve attachment 20. Those skilled in the art will readily appreciate that a vacuum can be maintained within the outer cannulation 36 during the transition from evacuating the air 152 from the outer cannulation 36 and the introduction of hydrating fluid 154 into the auxiliary syringe 140. In other examples, a secondary fluid delivery device (not specifically shown) can be used for hydrating the injectable material 24. Such a secondary fluid delivery device can be fluidly coupled to the valve attachment 20.

With reference to FIGS. 7 and 8, the hydrating fluid 154 can be injected through the female receiving portion 142 and subsequently through the injection port 116 of the valve attachment 20. The hydrating fluid 154 can be any suitable hydrating fluid. In some examples, the hydrating fluid 154 can contain patient marrow. The fluid 154 then can communicate around the annular channel 102 formed in the valve body 18 and enter the outer cannulation 36 through the second opening 44 around the tapered distal tip 122 of the locking member 22. Once the injectable material 24 has been sufficiently hydrated, the consistency of the injectable material 24 can become viscous or flowable.

Figure 9:
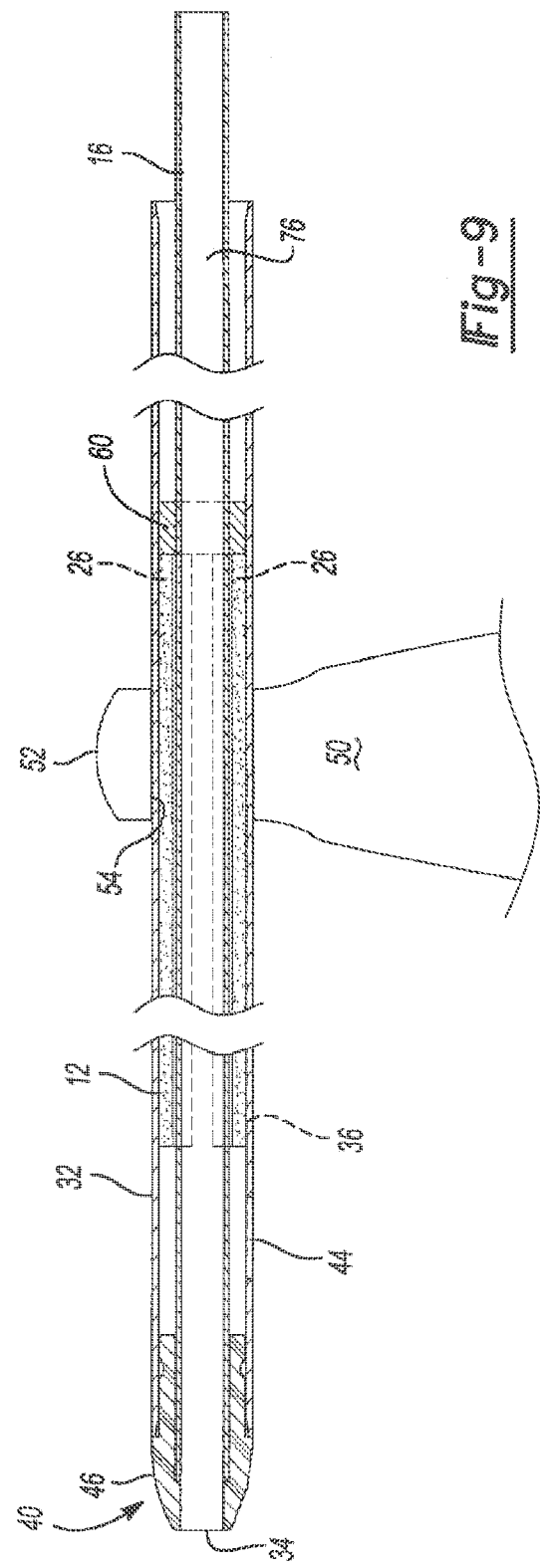
FIG. 9 is a cross-sectional view of the cannulated syringe shown with the valve body removed and the biologic material in a hydrated state.

With reference now to FIGS. 8 and 9, the surgeon can then remove the locking member 22 from the valve body 18 thereby unlocking the valve body 18 from the cannulated syringe 12. The valve body 18 can then be slidably translated along the distal end 40 toward the tapered distal tip 46 and off of the cannulated syringe 12. The plug 14 can also be slidably withdrawn from the proximal end 42 of the cannulated syringe 12.

With reference now to FIGS. 10 and 11, the inner cannulation 34 of the cannulated syringe 12 can be located onto a guide wire 160. The cannulated syringe 12 can then be advanced into an IM canal 162 of the tibia, such that the guide wire 160 slidably locates through the inner cannulation 34 of the cannulated syringe 12. The IM canal 162 is shown partially reamed. In this regard, a cannulated reaming bit (not shown) can be guided along the guide wire 160 as needed. The cannulated reaming bit can then be withdrawn from the IM canal 162 with the guide wire left in place. The guide wire, substantially undisturbed, can then be referenced by the cannulated syringe 12. It will be appreciated that the inner tube 30 of the cannulated syringe 12 can provide a barrier between the hydrated injectable material 24 and the guide wire 160.

Once the tapered distal tip 46 of the cannulated syringe 12 has been advanced to the desired location in the IM canal, the distal end 78 of the plunger 16 can be located into the outer cannulation 36 at the proximal end 42 of the cannulated syringe 12. Explained in greater detail, the tubular body 76 of the plunger 16 can be advanced toward the distal end 40 of the cannulated syringe 12 while the cannulation 82 of the plunger 16 receives the inner tube 30 of the cannulated syringe 12 (and the guide wire 160). As can be appreciated, the tubular body 76 can locate within the outer cannulation 36 of the cannulated syringe and expel the injectable material 24 through the second opening 44 as the plunger 16 progressively advances distally through the outer cannulation 36. A surgeon can grasp the handle 50 of the cannulated syringe 12 with one hand and grasp the gripping portion 84 of the plunger 16 with the other hand to manipulate the respective cannulated syringe 12 and plunger 16 in a desired manner.

Once the desired amount of injectable material 24 has been delivered to the delivery site, the plunger 16 together or in sequence with the cannulated syringe 12 can be withdrawn from the guide wire 160. Other steps may optionally be carried out using the guide wire 160 as reference. An implant, such as an IM nail can then be implanted. One exemplary IM nail is disclosed in U.S. Pat. No. 6,652,528, Vandewalle, issued Nov. 25, 2003 entitled "Intramedullary Nail with Modular Sleeve," the contents of which are expressly incorporated herein by reference. Other IM nails may also be used.

Non-Limiting Discussion of Terminology

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "desire" or "desirable" refer to embodiments of the technology that afford certain benefits, under certain circumstances. However, other embodiments may also be desirable, under the same or other circumstances. Furthermore, the recitation of one or more desired embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on", "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

What is claimed is:

1. A set of instruments configured to introduce an injectable material to a bone, the set of instruments comprising:
    a cannulated syringe extending along a longitudinal axis between a proximal and a distal end, the cannulated syringe having an inner tube and an outer tube that are fixedly interconnected at the distal end as a single unit, wherein a first cannulation is formed along the longitudinal axis of the cannulated syringe within the inner tube and a second cannulation is formed within an annular space between the inner and outer tubes, wherein the distal end of the cannulated syringe defines a first opening at an end of the inner tube and a second opening defined through a cylindrical sidewall of the outer tube, and wherein the cannulated syringe is closed from fluid communication between the inner and outer tubes;
    a tubular piston that surrounds the inner tube and is configured to slidably advance through the second cannulation in a direction toward the distal end in order to introduce the injectable material from the outer cannulation of the cannulated syringe to the bone through the second opening;
    a valve body having a central passage that is sized to slidably advance onto the distal end of the cannulated syringe, the valve body having a valve inlet formed therein, wherein the valve inlet is configured to fluidly connect with the second opening; and
    a valve attachment configured to be coupled to the valve body and defining an injection port that is configured to receive a fluid delivery device that can transfer a fluid through the second opening and into the outer cannulation, wherein the fluid is capable of hydrating the injectable material.

2. The set of instruments of claim 1 wherein the valve body includes a valve attachment mounting portion from which the valve inlet extends.

3. The set of instruments of claim 2 wherein the valve body includes a valve inlet body defining the valve inlet, and includes a cylindrical pocket on the valve attachment mounting portion surrounding the valve inlet body.

4. The set of instruments of claim 3 wherein the valve attachment mounting portion includes a valve mating portion that is configured to be advanced into a clearance fit with the valve inlet body.

5. The set of instruments of claim 4 wherein the valve mating portion, including an outer cylinder and an inner cylinder, wherein the outer cylinder is configured to locate into the cylindrical pocket of the valve attachment mounting portion.

6. The set of instruments of claim 5 wherein the valve inlet body is configured to locate into a cylindrical pocket defined in an annular space between the inner cylinder and the outer cylinder of the valve mating portion.

7. The set of instruments of claim 1 wherein the second opening comprises an oblong slot.

8. The set of instruments of claim 1 wherein the inner tube is longer than the outer tube such that the inner tube extends proud from the proximal end relative to the outer tube.

9. The set of instruments of claim 8 wherein the cannulated syringe includes a handle disposed on the proximal end that extends generally transverse to the longitudinal axis.

10. The set of instruments of claim 1 wherein the second opening is located proximate the first opening and within the distal most one-quarter of an entire length of the cannulated syringe.

11. The set of instruments of claim 1 further comprising:
    a plug configured to be advanced into the outer cannulation from the proximal end of the cannulated syringe, the plug having elastomeric seals that are configured to create a fluid tight seal in the outer cannulation and a central opening that slidably receives the inner tube.

12. The set of instruments of claim 11 wherein the plug includes a plug body that extends from a proximal end to a distal end, and includes a collar at the proximal end of the plug that has an outer diameter that is greater than the outer tube.

13. The set of instruments of claim 1 further comprising:
a guide wire extending from an intramedullary canal of the bone, wherein the guide wire is configured to be at least partially received through the inner cannulation of the cannulated syringe, and wherein the cannulated syringe can be advanced along the guide wire until an opening provided in the cannulated syringe is located proximate to a delivery site.

14. The set of instruments of claim 1 further comprising:
the fluid delivery device, wherein the fluid delivery device is configured to transfer the fluid through the second opening and into the outer cannulation.

15. The set of instruments of claim 1 wherein the hydrating fluid includes bone marrow.

16. The set of instruments of claim 1 wherein the injectable material is configured to become viscous or flowable when sufficiently hydrated.

17. The set of instruments of claim 1 further comprising:
a plunger having a tubular body that is configured to slidably advance the tubular piston through the second cannulation in the direction toward the distal end.

18. The set of instruments of claim 17 wherein the plunger has a gripping portion disposed on a proximal end thereof.

19. The set of instruments of claim 17 wherein the plunger is configured to be retractable toward the proximal end of the cannulated syringe in order to create a vacuum within the outer cannulation.

20. The set of instruments of claim 1 further comprising:
a locking member;
wherein the valve body includes a locking aperture formed through an outer surface thereof, the valve body is configured to be advanced onto the cannulated syringe such that the locking aperture is selectively aligned with the second opening, and the locking member is configured to selectively extend through the locking aperture of the valve body and into the second opening thereby inhibiting slidable translation of the valve body along the cannulated syringe.

* * * * *